United States Patent
Hirai et al.

(10) Patent No.: US 9,121,839 B2
(45) Date of Patent: Sep. 1, 2015

(54) ANALYZING SYSTEM, ANALYZING APPARATUS, CONTAINER, ANALYZING METHOD, PROGRAM, AND RECORDING MEDIUM

(75) Inventors: Mitsuharu Hirai, Kyoto (JP); Satoshi Majima, Kyoto (JP); Toshiya Hosomi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1072 days.

(21) Appl. No.: 13/145,774

(22) PCT Filed: Jan. 21, 2010

(86) PCT No.: PCT/JP2010/050725
§ 371 (c)(1),
(2), (4) Date: Jul. 21, 2011

(87) PCT Pub. No.: WO2010/084921
PCT Pub. Date: Jul. 29, 2010

(65) Prior Publication Data
US 2012/0021419 A1    Jan. 26, 2012

(30) Foreign Application Priority Data

Jan. 23, 2009 (JP) ................................ 2009-013706

(51) Int. Cl.
*G01N 21/75* (2006.01)
*G01N 35/00* (2006.01)
*B01L 3/00* (2006.01)
*G01N 35/02* (2006.01)

(52) U.S. Cl.
CPC ........ *G01N 35/00732* (2013.01); *B01L 3/5085* (2013.01); *B01L 3/527* (2013.01); *B01L 3/545* (2013.01); *G01N 21/75* (2013.01); *G01N 35/026* (2013.01); *B01L 2200/04* (2013.01); *B01L 2300/02* (2013.01); *B01L 2300/021* (2013.01); *B01L 2300/022* (2013.01); *B01L 2300/023* (2013.01); *B01L 2300/024* (2013.01); *B01L 2300/0829* (2013.01); *G01N 2035/00752* (2013.01)

(58) Field of Classification Search
CPC ....................................................... G01N 21/75
USPC ......................................................... 422/417
See application file for complete search history.

(56) References Cited

U.S. PATENT DOCUMENTS

| | | | | |
|---|---|---|---|---|
| 3,909,203 | A * | 9/1975 | Young et al. | 422/67 |
| 2002/0155616 | A1 | 10/2002 | Hiramatsu et al. | 436/165 |
| 2005/0003392 | A1* | 1/2005 | Salceda et al. | 435/6 |
| 2006/0000296 | A1* | 1/2006 | Salter | 73/863.01 |
| 2006/0120926 | A1 | 6/2006 | Takada et al. | |
| 2007/0148052 | A1 | 6/2007 | Hiramatsu et al. | 422/102 |
| 2008/0268529 | A1 | 10/2008 | Furusato et al. | |

FOREIGN PATENT DOCUMENTS

| | | | |
|---|---|---|---|
| CN | 1720168 A | 1/2006 | |
| CN | 1965073 A | 5/2007 | |
| JP | 3-181853 | 8/1991 | ........... G01N 33/543 |
| JP | 6-074958 | 3/1994 | ............. G01N 35/06 |
| JP | 8-122336 | 5/1996 | ............. G01N 35/02 |
| JP | 2001-349896 | 12/2001 | ............. G01N 35/02 |
| JP | 2004-354300 | 12/2004 | ............. G01N 33/53 |

OTHER PUBLICATIONS

Office Action issued in corresponding Japanese Patent Application No. 2010-526085 dated Sep. 10, 2013.
International Search Report for PCT/JP2010/050725 (mailed Apr. 20, 2010) with partial translation.

* cited by examiner

*Primary Examiner* — Ardin Marschel
(74) *Attorney, Agent, or Firm* — Morgan, Lewis & Bockius LLP

(57) ABSTRACT

An analyzing system that enables further expansion of analysis items and automation of analysis. In the analyzing system for performing an analysis using container 1 and an analyzing apparatus, container 1 is a dedicated container previously containing a reagent for a specific analysis item or an expansion container to which a user can freely set an analysis item.

14 Claims, 9 Drawing Sheets

FIG. 12

| Type of container | Analysis condition number | Analysis condition |
|---|---|---|
| Dedicated container | 1<br>2<br>3<br>.<br>.<br>. | $X_1 °C, \cdots$<br>$X_2 °C, \cdots$<br>$X_3 °C, \cdots$<br>.<br>.<br>. |
| Expansion container | $E_1$ | $E_{1a} : Y_1 °C, \cdots$<br>$E_{1b} : Y_2 °C, \cdots$<br>$E_{1c} : Y_3 °C, \cdots$ | ns
ANALYZING SYSTEM, ANALYZING APPARATUS, CONTAINER, ANALYZING METHOD, PROGRAM, AND RECORDING MEDIUM

CROSS-REFERENCE TO RELATED APPLICATION

This application is a 371 filing based on PCT/JP2010/050725, filed Jan. 21, 2010 which claims priority to Japanese Application No. JP 2009-013706, filed Jan. 23, 2009, all of which are hereby incorporated by reference in their entirety.

TECHNICAL FIELD

The present invention relates to an analyzing system, an analyzing apparatus, a container, an analyzing method, a program, and a recording medium.

BACKGROUND ART

An apparatus for analyzing a specific component in a sample has conventionally been used widely. An analyzing apparatus in which a sample (a specimen) such as blood or urine is reacted with a specific reagent, the reaction is detected by an optical manner or an electrochemical manner, and the detection result is output, is known in the field of clinical examination, for example. Such an analyzing apparatus can fall into two broad categories: a dedicated apparatus whose analyte is specified; and a general-purpose apparatus whose analyte (analysis item) can be freely set by a user. In the case of the dedicated apparatus, a cartridge-type container that has been previously filled with a necessary reagent is provided, an analysis condition that has been previously set has been input into the apparatus, and once the cartridge-type container and the sample are set into the dedicated apparatus, the apparatus can automatically perform a series of steps of sampling the sample, reacting the sample with the reagent, detecting the reaction, and outputting the detection result. In contrast, in the case of the general-purpose apparatus, a user is required to set a necessary reagent into the apparatus and to input an analysis condition into the same. That is, while the dedicated apparatus has an advantage in that an analysis can be performed automatically, it also has a problem in that an analysis item is limited and cannot be expanded. In contrast, although an analysis by the general-purpose apparatus is performed manually and has a problem in analysis efficiently, the general-purpose apparatus has an advantage in that an analysis item can be set freely. Therefore, conventionally, it has been necessary to have both the dedicated apparatus and the general-purpose apparatus in order to realize high analysis efficiency and an expansion of an analysis item. However, in order to have both the dedicated apparatus and the general-purpose apparatus, costs are involved, and a large analyzing space is required.

In order to solve this problem, an analyzing apparatus having functions of both the dedicated apparatus and the general-purpose analyzing apparatus has been proposed (see JP 2001-349896 A). In this analyzing apparatus, a cartridge-type dedicated container that has been previously filled with a specific reagent and a general-purpose cartridge-type container that is empty and in which a user can freely fill a reagent can be used distinctively. The cartridge-type dedicated container is sealed, and on the seal, a bar code including an analysis condition is printed. In contrast, the general-purpose cartridge-type container is not sealed. When a cartridge-type container is set in an analyzing apparatus, the analyzing apparatus determines whether the container is a cartridge-type dedicated container or a general-purpose cartridge-type container by determining whether or not the container is sealed. When it is determined that the container is the cartridge-type dedicated container, an analysis is automatically performed under the condition that is previously set in the analyzing apparatus. On the other hand, when it is determined that the container is a general-purpose cartridge-type container, a user selects an analysis item, an analysis condition for the analysis item selected is read from a storage apparatus, and an analysis is performed under the analysis condition read.

DISCLOSURE OF THE INVENTION

Problem to be Solved by the Invention

The analyzing apparatus has an advantage in having functions of both the dedicated apparatus and the general-purpose apparatus. However, there is a demand on the analyzing apparatus to further expand analysis items and further automate an analysis.

Hence, the present invention is intended to provide an analyzing system that enables further expansion of analysis items and automation of analysis, an analyzing apparatus, a container, an analyzing method, a program, and a recording medium.

Means for Solving Problem

In order to achieve the aforementioned object, the analyzing system of the present invention is an analyzing system including: a container; and an analyzing apparatus. The container is a dedicated container previously containing a specific reagent for an analysis item or an expansion container to which a user can freely set an analysis item. Each of the dedicated container and the expansion container includes an information label. The information label includes analysis condition information. The analysis condition information is information by which it can be determined whether the container is the dedicated container or the expansion container. The analyzing apparatus includes: a label reading device for reading information on the information label; and a controlling device for controlling an analysis condition. The label reading device reads information on the information label, and the controlling device determines whether the container is the dedicated container or the expansion container on the basis of the analysis condition information of the information label read.

The analyzing apparatus of the present invention is an analyzing apparatus used in the analyzing system of the present invention, including: a label reading device for reading information on the information label included in the container; and a controlling device for controlling an analysis condition. The label reading device reads information on the information label, and the controlling device determines whether the container is the dedicated container or the expansion container on the basis of the analysis condition information of the information label read.

The container of the present invention is a container used in the analyzing system of the present invention. The container is a dedicated container previously containing a reagent for a specific analysis item or an expansion container to which a user can freely set an analysis item. Each of the dedicated container and the expansion container includes an information label. The information label includes analysis condition information. The analysis condition information is information by which whether the container is the dedicated container or the expansion container can be determined.

The analyzing method of the present invention is an analyzing method, including performing an analysis using a container and an analyzing apparatus. The container is a dedicated container previously containing a reagent for a specific analysis item or an expansion container to which a user can freely set an analysis item. Each of the dedicated container and the expansion container includes an information label. The information label includes analysis condition information. The analysis condition information is information by which whether the container is the dedicated container or the expansion container can be determined. The analyzing apparatus includes: a label reading device for reading information on the information label; and a controlling device for controlling an analysis condition. The information label reading device reads information on the information label, and the controlling device determines whether the container is the dedicated container or the expansion container on the basis of the analysis condition information on the information label read.

The program of the present invention is a program that can execute the analyzing method of the present invention in the analyzing apparatus.

The recording medium of the present invention is a recording medium recording the program of the present invention.

Effects of the Invention

In the present invention, whether the container is the dedicated container or the expansion container is determined based on the analysis condition information on the information label included in the container. The information label of the expansion container, therefore, also includes analysis condition information, which enables expansion of analysis items and automation of analysis.

BRIEF DESCRIPTION OF DRAWINGS

FIG. 12 is a table showing an example of a configuration of analysis condition information of the present invention.

BEST MODE FOR CARRYING OUT THE INVENTION

Figure 1:
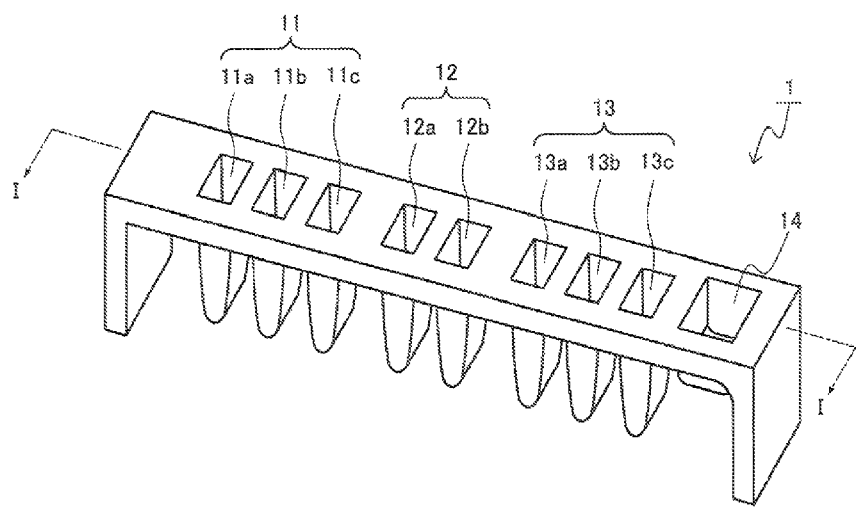
FIG. 1 is a perspective view showing an example of a configuration of a container used in the analyzing system of the present invention.

It is preferable that in the analyzing system of the present invention, the analysis condition information includes an analysis condition number and an analysis condition associated with the analysis condition number, a corresponding analysis condition number is assigned to each of the dedicated container and the expansion container, and the controlling device determines whether the container is the dedicated container or the expansion container on the basis of the analysis condition number. According to this analyzing system, distinguishing between the dedicated container and the expansion container can be performed quickly and easily.

It is preferable that in the analyzing system of the present invention, the analyzing apparatus further includes an analysis condition information storing device for storing analysis condition information with respect to each analysis item, when the controlling device determines that the container is the dedicated container, the analysis condition information that is previously stored is retrieved from the analysis condition information storing device, and control information is output in accordance with the analysis condition information retrieved, when the controlling device determines that the container is the expansion container, whether or not the analysis item set by the user is the first-time analysis item is determined. When it is determined that the analysis item is the first-time analysis item, analysis condition input request information is output, and the analysis condition information input in accordance with the output information is stored in the analysis condition information storing device. When it is determined that the analysis item is not the first-time analysis item, control information is output in accordance with the analysis condition information stored in the analysis condition storing device. This analyzing system enables an analysis to be automated considerably.

It is preferable that in the analyzing system of the present invention, the analyzing apparatus further includes an input device for inputting information from outside of the analyzing apparatus, and the analysis condition information is input by the input device.

It is preferable that in the analyzing system of the present invention, the analyzing apparatus further includes an information retrieving device, the analysis condition information outside of the analyzing apparatus is retrieved through a communication network outside of the system by the information retrieving device in accordance with the analysis condition input request information, and the analysis condition information retrieved is input. This analyzing system enables an analysis to be automatically immediately performed even in the case where the analysis item is an item selected by a user for the first time.

It is preferable that the analyzing system further includes a server, and the analysis condition information outside of the analyzing apparatus is stored in the server.

It is preferable that in the analyzing system, the analyzing apparatus further includes an information transmitting device, and analysis condition information that is related to an analysis item set by a user can be stored in the server through the communication network by the information transmitting device. This analyzing system enables other users to use analysis condition information set by a user, and enables further automation of analysis as viewed from a whole system.

It is preferable that in the analyzing system of the present invention, the expansion container includes a common reagent bath that has been filled with a common reagent that can be used in common and a specific reagent bath that can be filled with a specific reagent that is required to be specifically provided depending on an analysis item set by a user. According to this analyzing system, users can save their works to prepare common reagents. Thus, analysis efficiency is improved.

It is also preferable that in the analyzing system, a specific reagent bath of the expansion container is previously filled with a specific reagent. According to this analyzing apparatus, users can save their works by, for example, filling the specific reagent bath with a specific reagent by a provider of the container in response to requests from the users. Thus, analysis efficiency is further improved.

It is preferable that, in the analyzing system, in the case where an analyte is a gene, the common reagent contains DNA polymerase and dNTP, and the specific reagent contains a primer. Further, the specific reagent may further contain a probe, an intercalater, and the like.

It is preferable that in the analyzing system of the present invention, each of the dedicated container and the expansion container is a cartridge-type container.

It is preferable that the analyzing system of the present invention further includes a specific reagent container to be filled with a specific reagent that is required to be specifically provided depending on an analysis item set by a user, and the analyzing apparatus includes the cartridge-type container setting part and the specific reagent container setting part. This analyzing system enables a reduction in dead volume of the reagent as described below.

It is preferable that in the analyzing apparatus of the analyzing system, the cartridge-type expansion container is set in the cartridge-type container setting part, the specific reagent container is set in the specific reagent container setting part, the cartridge-type expansion container includes a common reagent bath that has been filled with a common reagent that can be used in common, and the specific reagent container is filled with the specific reagent.

It is preferable that in the analyzing system of the present invention, the information label is a bar code or a two-dimensional code.

It is preferable that in the analyzing apparatus of the present invention, the analysis condition information includes an analysis condition number and an analysis condition associated with the analysis condition number, a corresponding analysis condition number is assigned to each of the dedicated container and the expansion container, and the controlling device determines whether the container is the dedicated container or the expansion container on the basis of the analysis condition number.

It is preferable that the analyzing apparatus further includes an analysis condition information storing device for storing analysis condition information with respect to each analysis item, when the controlling device determines that the container is the dedicated container, the analysis condition information that is previously stored is retrieved from the analysis condition information storing device, and control information is output in accordance with the analysis condition information retrieved, when the controlling device determines that the container is the expansion container, whether or not the analysis item set by the user is the first-time analysis item is determined, when it is determined that the analysis item is the first-time analysis item, analysis condition input request information is output, and the analysis condition information input in accordance with the output information is stored in the analysis condition information storing device, and when it is determined that the analysis item is not the first-time analysis item, control information is output in accordance with the analysis condition information stored in the analysis condition storing device.

It is preferable that the analyzing apparatus of the present invention further includes an input device for inputting information from outside of the apparatus, and the analysis condition information is input by the input device.

It is preferable that the analyzing apparatus of the present invention further includes an information retrieving device, the analysis condition information outside of the analyzing apparatus is retrieved through a communication network outside of the system by the information retrieving device in accordance with the analysis condition input request information, and the analysis condition information retrieved is input.

It is preferable that in the analyzing apparatus, the analysis condition information outside of the analyzing apparatus is stored in a server outside of the analyzing apparatus.

It is preferable that the analyzing apparatus further includes an information transmitting device, analysis condition information that is related to an analysis item set by a user can be stored in the server through the communication network by the information transmitting device.

In the analyzing apparatus of the present invention, an analyte is, for example, a gene.

The analyzing apparatus of the present invention is, for example, preferably a cartridge-type container capable type.

It is preferable that in the analyzing apparatus of the present invention, a specific reagent container to be filled with a specific reagent that is required to be specifically provided depending on an analysis item set by a user can be used, and the analyzing apparatus further includes the cartridge-type container setting part and the specific reagent container setting part.

It is preferable that, in the analyzing apparatus, the cartridge-type expansion container is set in the cartridge-type container setting part, the specific reagent container is set in the specific reagent container setting part, the cartridge-type expansion container includes a common reagent bath that has been filled with a common reagent that can be used in common, and the specific reagent container is filled with the specific reagent.

It is preferable that in the analyzing apparatus of the present invention, the label reading device is a bar code reader.

It is preferable that in the container of the present invention, the analysis condition information includes an analysis condition number and an analysis condition associated with the analysis condition number, a corresponding analysis condition number is assigned to each of the dedicated container and the expansion container, and whether the container is the dedicated container or the expansion container can be determined on the basis of the analysis condition number.

It is preferable that in the container of the present invention, the expansion container includes a common reagent bath that has been filled with a common reagent that can be used in common and a specific reagent bath that can be filled with a specific reagent that is required to be specifically provided depending on an analysis item set by a user.

In the container, a specific reagent bath of the expansion container may be previously filled with a specific reagent.

In the container, for example, an analyte may be a gene, the common reagent may contain DNA polymerase and dNTP, and the specific reagent may contain a primer.

It is preferable that in the container of the present invention, each of the dedicated container and the expansion container is a cartridge-type container.

It is preferable that a specific reagent container to be filled with a specific reagent that is required to be specifically provided depending on an analysis item set by a user is included as the container of the present invention.

The container of the present invention may be configured so that the cartridge-type expansion container includes a common reagent bath that has been filled with a common reagent that can be used in common, and the specific reagent container is filled with the specific reagent.

It is preferable that in the container of the present invention, the information label is a bar code or a two-dimensional code.

It is preferable that in the analyzing method of the present invention, the analysis condition information includes an analysis condition number and an analysis condition associated with the analysis condition number, a corresponding analysis condition number is assigned to each of the dedicated container and the expansion container, and the controlling device determines whether the container is the dedicated container or the expansion container on the basis of the analysis condition number.

It is preferable that in the analyzing method of the present invention, the analyzing apparatus further includes an analysis condition information storing device for storing analysis condition information with respect to each analysis item. When the controlling device determines that the container is the dedicated container, the analysis condition information that is previously stored is retrieved from the analysis condition information storing device, and control information is output in accordance with the analysis condition information retrieved. When the controlling device determines that the container is the expansion container, whether or not the analysis item set by the user is the first-time analysis item is determined. When it is determined that the analysis item is the first-time analysis item, analysis condition input request information is output, and the analysis condition information input in accordance with the output information is stored in the analysis condition information storing device, and when it is determined that the analysis item is not the first-time analysis item, control information is output in accordance with the analysis condition information stored in the analysis condition storing device.

It is preferable that in the analyzing method of the present invention, the analyzing apparatus further includes an input device for inputting information from outside of the analyzing apparatus, and the analysis condition information is input by the input device.

It is preferable that in the analyzing method of the present invention, the analyzing apparatus further includes an information retrieving device, the analysis condition information outside of the analyzing apparatus is retrieved through the communication network outside of the system by the information retrieving device in accordance with the analysis condition input request information, and the analysis condition information retrieved is input.

It is preferable that in the analyzing method, a server is used, and the analysis condition information outside of the analyzing apparatus is stored in the server.

It is preferable that in the analyzing method, the analyzing apparatus further includes an information transmitting device, and analysis condition information relating to an analysis item set by a user is stored in the server through the communication network by the information transmitting device.

It is preferable that in the analyzing method of the present invention, the expansion container includes a common reagent bath that has been filled with a common reagent that can be used in common and a specific reagent bath that can be filled with a specific reagent that is required to be specifically provided depending on an analysis item set by the user.

In the analyzing method, a specific reagent bath of the expansion container may be previously filled with a specific reagent.

In the analyzing method of the present invention, an analyte may be a gene, the common reagent may contain DNA polymerase and dNTP, and the specific reagent may contain a primer, for example.

It is preferable that in the analyzing method of the present invention, each of the dedicated container and the expansion container is a cartridge-type container.

In the analyzing method of the present invention, a specific reagent container to be filled with a specific reagent that is required to be specifically provided depending on an analysis item set by a user may further be used, and the analyzing apparatus may include the cartridge-type container setting part and the specific reagent container setting part.

It is preferable that in the analyzing method, the cartridge-type expansion container includes a common reagent bath that has been filled with a common reagent that can be used in common, the specific reagent container has been filled with the specific reagent, and in the analyzing apparatus, the cartridge-type expansion container is set in the cartridge-type container setting part, the specific reagent container is set in the specific reagent container setting part, and an analysis is performed using the common reagent in the cartridge-type container and the specific reagent in the specific reagent container.

It is preferable that in the analyzing method of the present invention, the information label is a bar code or a two-dimensional code.

EXAMPLES

Next, the present invention is described with reference to the examples. It is to be noted that the present invention is not limited by the following examples.

Example 1

Figure 2:
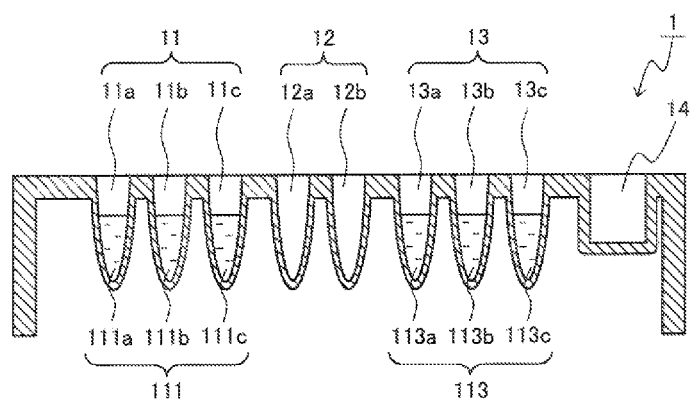
FIG. 2 is a sectional view taken along the line I-I of the container shown in FIG. 1.
Figure 3:
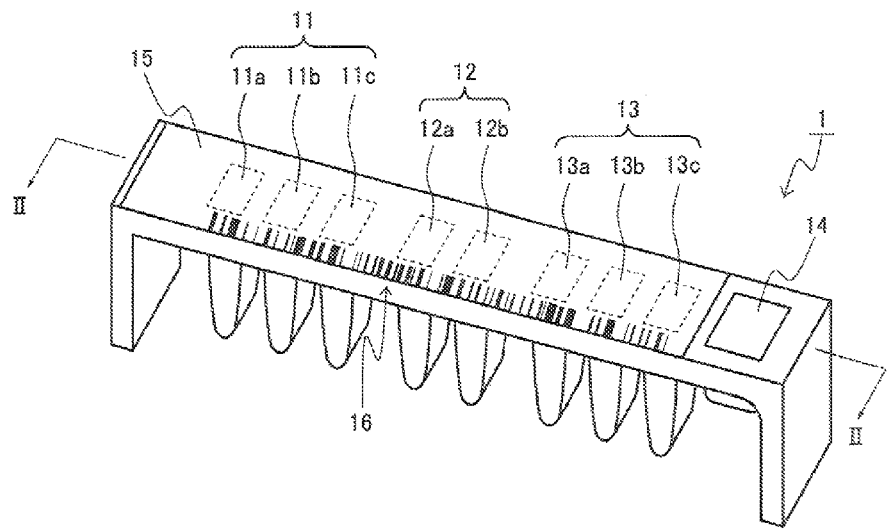
FIG. 3 is a perspective view showing another example of a configuration of a container used in the analyzing system of the present invention.
Figure 4:
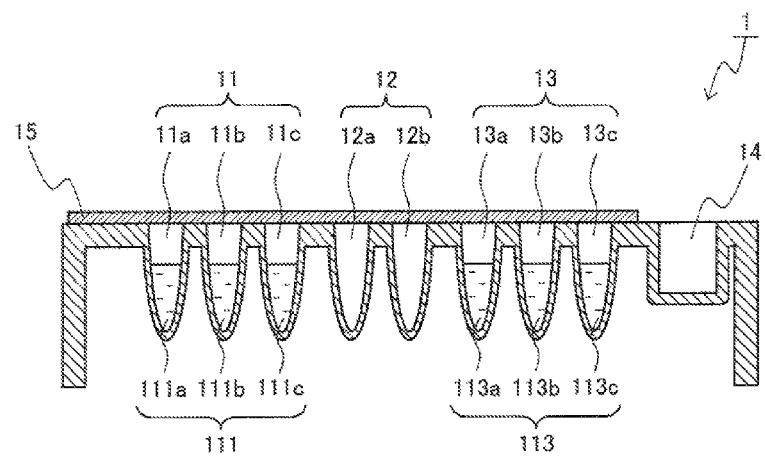
FIG. 4 is a sectional view taken along the line II-II of the container shown in FIG. 3.

The example of a container used in the analyzing system of the present invention is shown in FIGS. 1 to 4. FIG. 1 is a perspective view of the container of the present example. FIG. 2 is a sectional view taken along the line I-I of FIG. 1. FIG. 3 is a perspective view of the container of FIG. 1 in a state of being sealed. FIG. 4 is a sectional view taken along the line II-II of FIG. 3. In FIGS. 1 to 4, the parts identical to one another are denoted by the identical reference numerals.

A container of the present example in a state of not being sealed is shown in FIGS. 1 and 2. As shown in FIGS. 1 and 2, the container 1 is a cartridge-type container, and includes a common reagent bath 11 to be filled with a common reagent 111, an operation bath 12 to be used for operations such as a reaction and a dilution, a specific reagent bath 13 to be filled with a specific reagent 113, and a sample bath 14 to be filled with a sample (a specimen). The common reagent bath 11 is divided into three baths 11a, 11b, and 11c, which has been filled with three common reagents 111a, 111b, and 111c, respectively. The specific reagent bath 13 is divided into three baths 13a, 13b, and 13c, which are filled with three specific reagents 113a, 113b, and 113c, respectively. In the case of a cartridge-type dedicated container, a specific reagent bath is previously filled with a specific reagent by a provider who provides the container (hereinafter referred to as a container provider), and the container is supplied to a user. On the other hand, in the case of a cartridge-type expansion container, a user fills the specific reagent bath with the specific reagent in the analysis. It is to be noted that, even in the case of the cartridge-type expansion container, when a user requests a container provider to previously fill the specific reagent bath with the specific reagent, the cartridge-type expansion container in the state where the specific reagent bath is filled with the specific reagent is provided to the user. Further, as mentioned below, in the case where a specific reagent container is used besides the cartridge-type container, the specific reagent bath of the cartridge-type expansion container is not filled with the specific reagent, and the specific reagent container is filled with the specific reagent. A user may fill the specific reagent container with a specific reagent in the analysis, or a container provider may previously fill the same in response to the user's request.

A container of the present example in a state of being sealed is shown in FIGS. 3 and 4. As shown in FIGS. 3 and 4, the container is sealed with a seal 15 so that upper openings of the common reagent bath 11, the operation bath 12, and the specific reagent bath 13 are sealed, but the upper opening of the sample bath 14 is opened. An information label (a bar code) 16 is printed on a part of the surface of the seal 15. The bar code 16 represents analysis condition information. Examples of the analysis condition information include an analysis condition number and an analysis condition associated with the analysis condition number. Assigning a corresponding analysis condition number to each of the dedicated container and the expansion container enables determining whether the container is the dedicated container or the expansion container as well as specifying and retrieving analysis condition information by recognizing the analysis condition number. Information represented by the bar code 16 is not limited to the analysis condition information, and the bar code 16 may represent other information. Examples of the other information include an analysis item, a production date of a reagent, expiration date of the reagent, a lot number, a product number, and client information.

In the present invention, a material of the container is not particularly limited, and can be, for example, a conventional plastic. In the case where an analysis is performed by an optical method, it is required that at least whole or a part of a measurement part of the container is transparent. Thus, it is preferable that a transparent plastic such as polystyrene is used to the part to be transparent.

Figure 5:
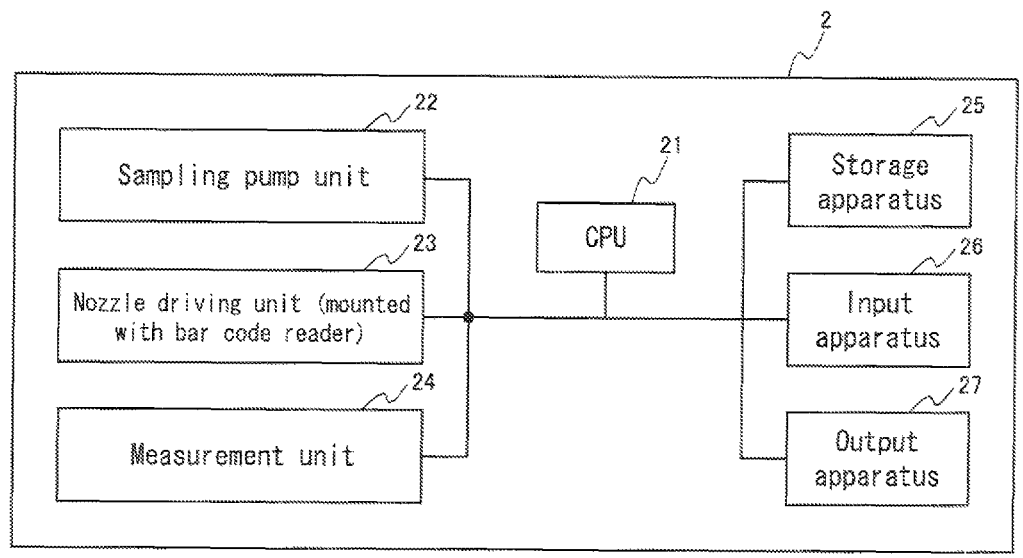
FIG. 5 is a block diagram showing an example of a configuration of the analyzing apparatus used in the analyzing system of the present invention.

Next, with reference to FIG. 5, the example of the analyzing apparatus of the present invention is explained. FIG. 5 is a block diagram showing a configuration of the analyzing apparatus of the present example. As shown in FIG. 5, the analyzing apparatus 2 of the present example includes, as main components, a central processing unit (a CPU) 21, a sampling pump unit 22, a nozzle driving unit 23, a measurement unit 24, a storage apparatus 25, an input apparatus 26, and an output apparatus 27. The CPU 21 controls movements of the sampling pump unit 22, the nozzle driving unit 23, and the measurement unit 24. The sampling pump unit 22 drives a pump to be used to sample a sample and a reagent, for example. The nozzle driving unit 23 moves a nozzle to each of the baths of the cartridge-type container, and moves the nozzle up and down. A bar code reader is mounted in the nozzle driving unit 23. The measurement unit 24 measures a reaction of the sample with the reagent. Examples of a method for measuring a reaction include an optical method and an electrochemical method. In the case of the optical method, the measurement unit 24 includes, for example, a light source and a light receiving part. In the case of the electrochemical method, the measurement unit 24 includes, for example, electrodes. The storage apparatus 25 stores, for example, analysis condition information, other information, and various programs, and is configured by combining, for example, a flash memory, a RAM, and a ROM, as appropriate. The input apparatus 26 is used to input information into the analyzing apparatus, and examples thereof include terminals such as a keyboard, a key sheet, and a USB and drives such as a CD and a CD-R. The output apparatus 27 is used to output analysis results and other information, and examples thereof include a printer and a display. The respective components of the present example may be combined in one body, or may be configured in multiple apparatuses. For example, an analyzing apparatus including the sampling pump unit 22, the nozzle driving unit 23, and the measurement unit 24 may be combined with a personal computer (PC) including the CPU 21, the storage apparatus 25, the input apparatus 26, and the output apparatus 27. In the case where an analysis using an expansion container is used in an analysis, and the analysis item is the first-time analysis item, information to request inputting analysis condition information is output from the output device by the CPU of the analyzing apparatus of the present example. Then, the analysis condition information that is input by the input device is automatically stored in the storage apparatus by the CPU, and used in the future analyses.

An example of controlling an analysis in the analyzing apparatus of the present example is explained by taking the case in which an analyte is a gene as an example. In the cartridge-type container, the common reagent bath 11 is filled with dNTP, polymerase, and other reagent, and the specific reagent bath 13 is filled with a primer and a probe. First, a user introduces a sample (a specimen) into a sample (a specimen) bath 14 of the cartridge-type container. Once this cartridge-type container is set in the analyzing apparatus, a nozzle automatically moves and samples a sample in the sample bath 14, then breaks the seal 15, and introduces the sample into the operation bath 12. Thereafter, the nozzle automatically moves, breaks the seal 15, and samples dNTP, polymerase, and a primer, and then introduces them into the operation bath 12. Thus, they react with the sample. In the case where the reaction is a PCR, a temperature cycle is controlled by the measurement unit 24. After the certain number of cycles of reactions, a probe in a reactant is detected by an optical manner.

Examples of the analyte of the present invention other than genes include biomolecules such as proteins (for example, enzymes, antigens, and antibodies) and lipid; organic molecules other than biomolecules; and inorganic molecules.

Figure 8:
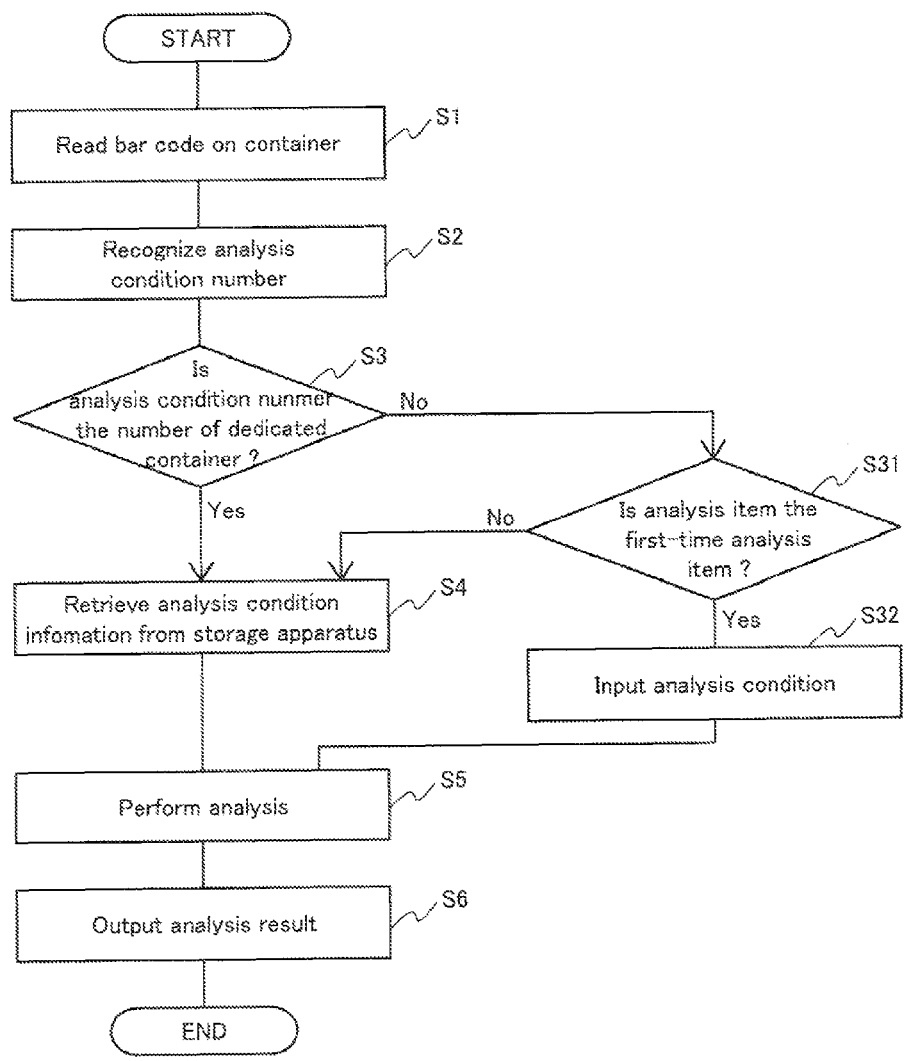
FIG. 8 is a flowchart showing an example of the analyzing system of the present invention.

With reference to a flowchart of FIG. 8, the example of an analysis using the cartridge-type container and the analyzing apparatus is explained.

A cartridge-type container is set in an analyzing apparatus. Then, a bar code on the container is read by a bar code reader (S1), and an analysis condition number is recognized (S2). Next, the analysis condition number is referred to with analysis condition information that is stored in the storage apparatus, and whether or not the container is a cartridge-type dedicated container is determined (S3). An example of the analysis condition information that is stored in the storage apparatus is shown in a table of FIG. 12. As shown in FIG. 12, in this table, the type of the container, an analysis condition number, and an analysis condition that are associated with one another are stored. As shown in FIG. 12, for example, analysis condition Nos. 1, 2, and 3 are numbers assigned to the respective dedicated containers. Thus, in the case where an analysis condition number in the bar code (see FIG. 3) on the container is 1, in the analyzing apparatus, it is determined that the container is a dedicated container (Yes), an analysis condition (for example, a temperature of $X_1°$ C.) of the analysis condition No. 1 is retrieved (S4), and an analysis is performed by a CPU under this condition (S5). Similarly, in the case where the analysis condition number is 2, in the analyzing apparatus, it is determined that the container is a dedicated container, an analysis condition (for example, a temperature of $X_2°$ C.) of the analysis condition No. 2 is specified. Further, in the case where the analysis condition number is 3, in the analyzing apparatus, it is determined that the container is a dedicated container, and an analysis condition (for example, a temperature of $X_3°$ C.) of the analysis condition No. 3 is specified. Then, analyses are controlled by the CPU under the respective conditions. On the other hand, in the table of FIG. 12, an analysis condition No. E1 (for example, a numeral of 100) is assigned to a cartridge-type expansion container. In the case where the analysis condition number is E1, in the analyzing apparatus, it is determined that the container is not a dedicated container (No) (S3), in other word, it is determined that the container is an expansion container (S3). In the case where the container is an expansion container, whether or not the analysis item specified is the first-time analysis item is determined (S31). In the case where the analysis item is not the first-time analysis item (No, in the case where analysis was performed with respected to the analysis item by the analyzing apparatus before), analysis condition information is retrieved from the storage apparatus (S4), and an analysis is performed by the CPU under this condition (S5). In contrast, in the case where the analysis item is the first-time analysis item (Yes), information to request inputting analysis condition information is output to an output apparatus by the CPU. A user inputs the analysis condition information by an input apparatus in accordance with the request. Since three analysis conditions E1$a$, E1$b$, and E1$c$ are stored to the analysis condition No. E1 of the expansion container in the case of the table of FIG. 12, these analysis conditions are output to the output apparatus. A user specifies an analysis condition from these analysis conditions by an input apparatus. Thus, analysis condition information can be input. For example, by specifying the analysis condition E1$a$, an analysis conditions such as a temperature $Y_1°$ C. and the like are input automatically. The analysis condition information input is automatically stored in the storage apparatus by the CPU for the future analyses. Then, after performing the analysis, an analysis result is output from the output apparatus (S6). In the present example, a user inputs analysis condition information, but the present invention is not limited to this. For example, a provider of the analyzing apparatus or the container may record analysis condition information in a recording medium (for example, a CD, a USB, or a memory), and may provide this recording medium to a user.

Example 2

Figure 6:
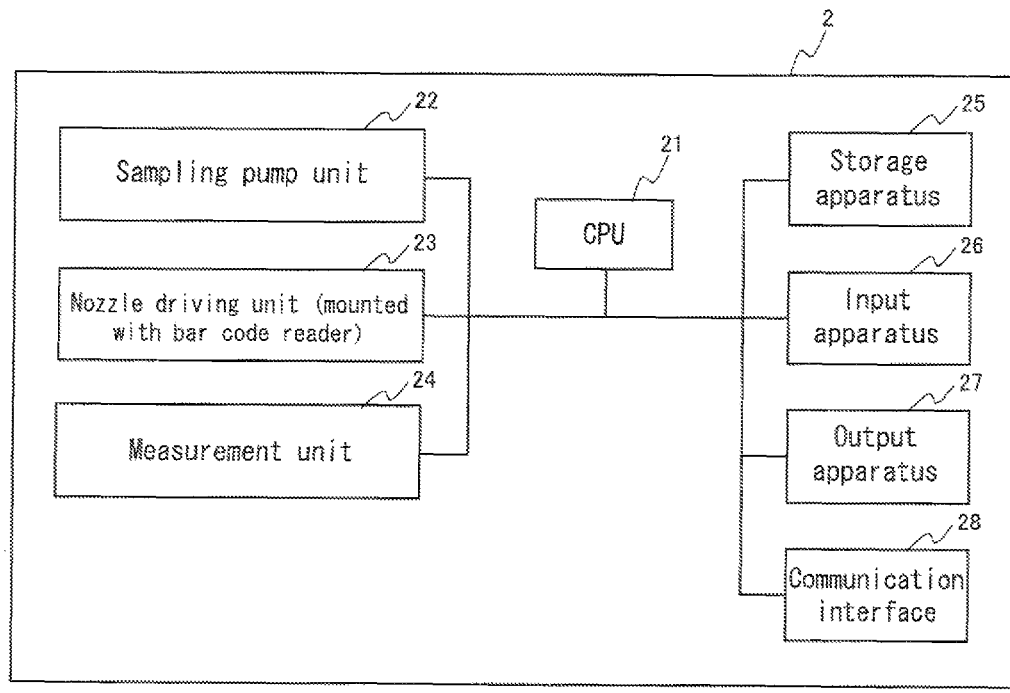
FIG. 6 is a block diagram showing another example of a configuration of the analyzing apparatus used in the analyzing system of the present invention.
Figure 7:
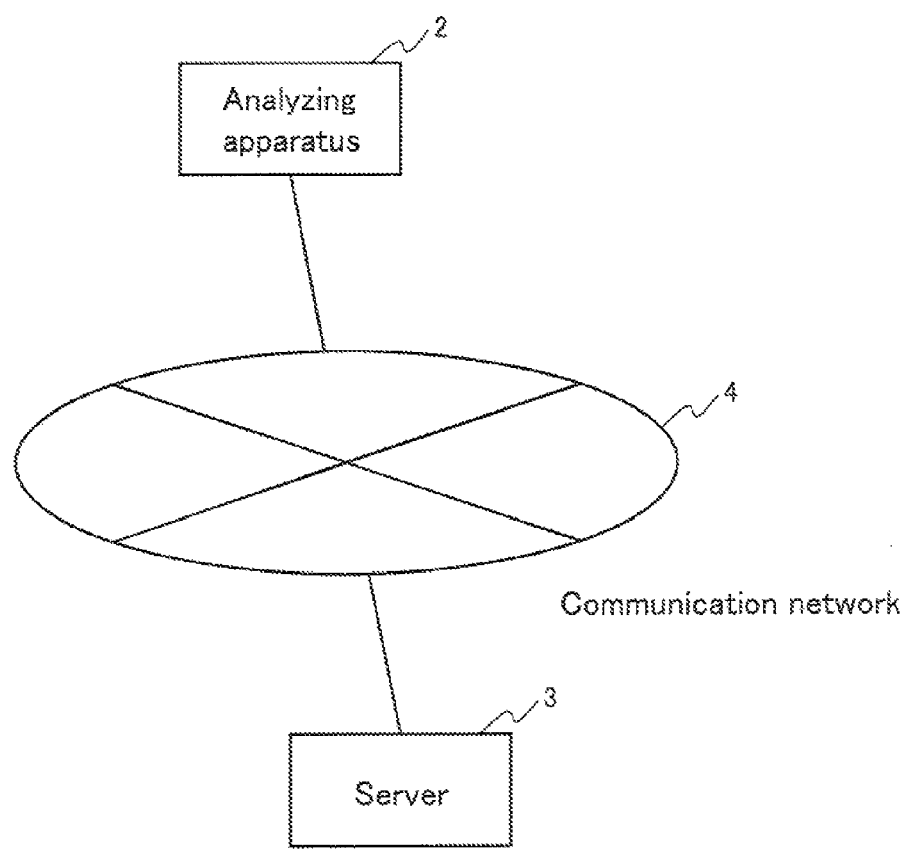
FIG. 7 is a schematic view showing an example of the analyzing system of the present invention.

Next, with reference to FIG. 6, the example of an analyzing apparatus that can connect to a server outside of the apparatus through a communication network (for example, the Internet) outside of the system is explained. In FIG. 6, the parts identical to those in FIG. 5 are denoted by the identical reference numerals. As shown in FIG. 6, the analyzing apparatus of the present example includes a communication interface 28, and an information retrieval unit (a search program) is stored in a storage apparatus 25. As shown in FIG. 7, an analyzing apparatus 2 of the present example can connect to a server 3 outside of the apparatus through a communication network 4. In the analyzing apparatus of the present example, the other configuration is the same as that of the analyzing apparatus of Example 1.

Figure 9:
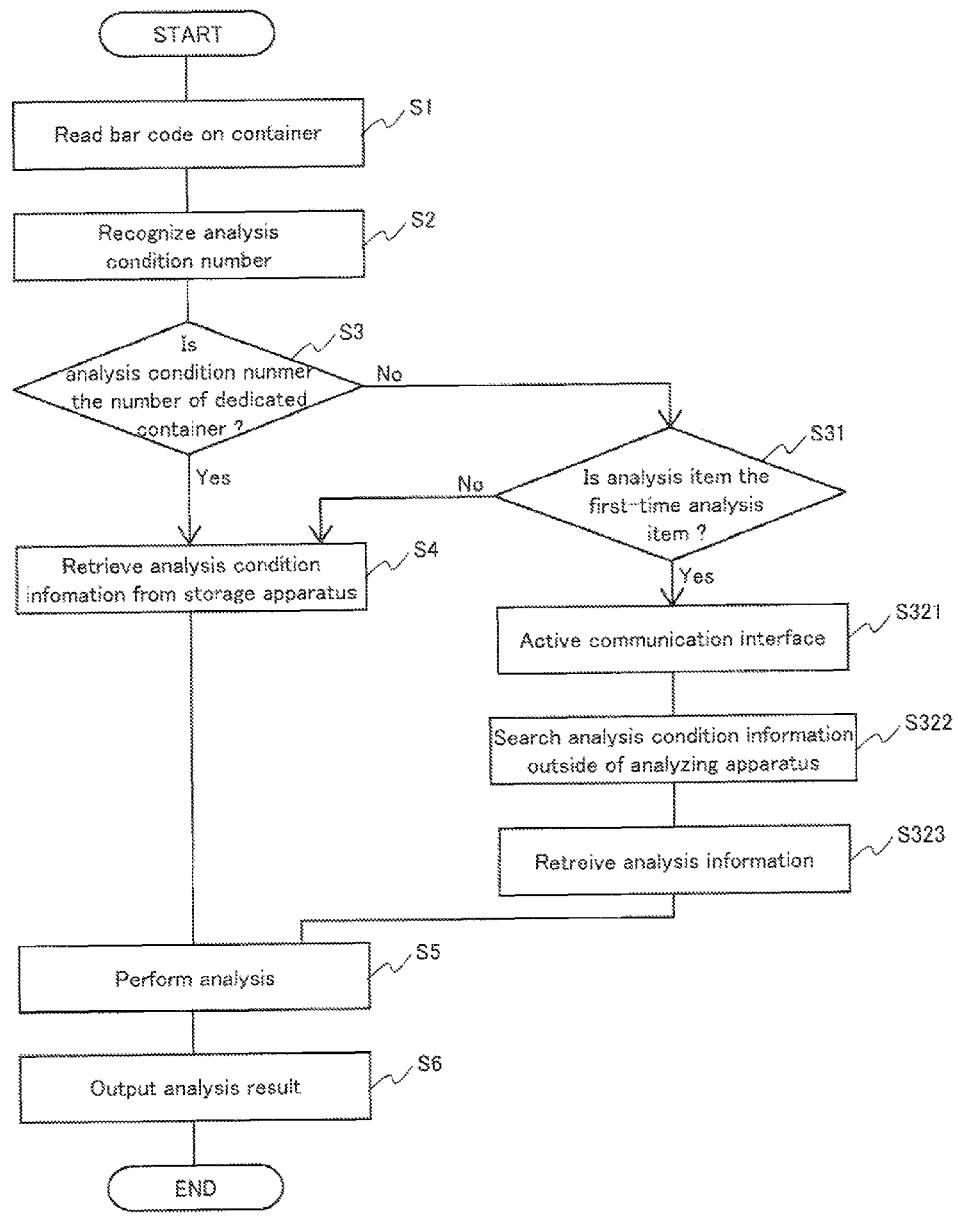
FIG. 9 is a flowchart showing another example of the analyzing system of the present invention.

With reference to a flowchart of FIG. 9, a procedure of analysis using the cartridge-type container and the analyzing apparatus of the present example is explained. In FIG. 9, the parts identical to those in FIG. 8 are denoted by the identical reference numerals. The procedure of analysis of the present example is the same as that of Example 1 except that in the analyzing apparatus, in the case where it is determined that the container is an expansion container, and the analysis item is the first-time analysis item, analysis condition information is automatically searched and retrieved, and the analysis is performed in accordance with the analysis condition information retrieved. That is, when it is determined that the container is an expansion container from a bar code (S3), it is subsequently determined whether or not the analysis item is the first-time analysis item (S31). Then, when it is determined that the analysis item is not the first-time analysis item (No), analysis condition information is retrieved from the storage apparatus (S4), the analysis is performed (S5), and an analysis result is output (S6). On the other hand, when it is determined that the analysis item is the first-time analysis item (Yes), a communication interface is activated by a CPU, and an information retrieving device (a search program) in the storage apparatus is read into the CPU and run (S321). The information retrieving device automatically accesses to a server outside of the apparatus through a communication network (the Internet) and searches (S322), and then retrieves analysis condition information in the server (S323). Subsequently, an analysis is performed in accordance with the analysis condition information retrieved (S5), and an analysis result is output (S6). The server is not particularly limited, and may be a server to which a public research organization such as a university uploads research information, or a server managed by a provider of the analyzing apparatus or the container. According to the present example, even in the case where a user sets a new analysis item, analysis condition information can be automatically retrieved. Thus, automation of the analyzing apparatus can be further progressed.

Example 3

Figure 10:
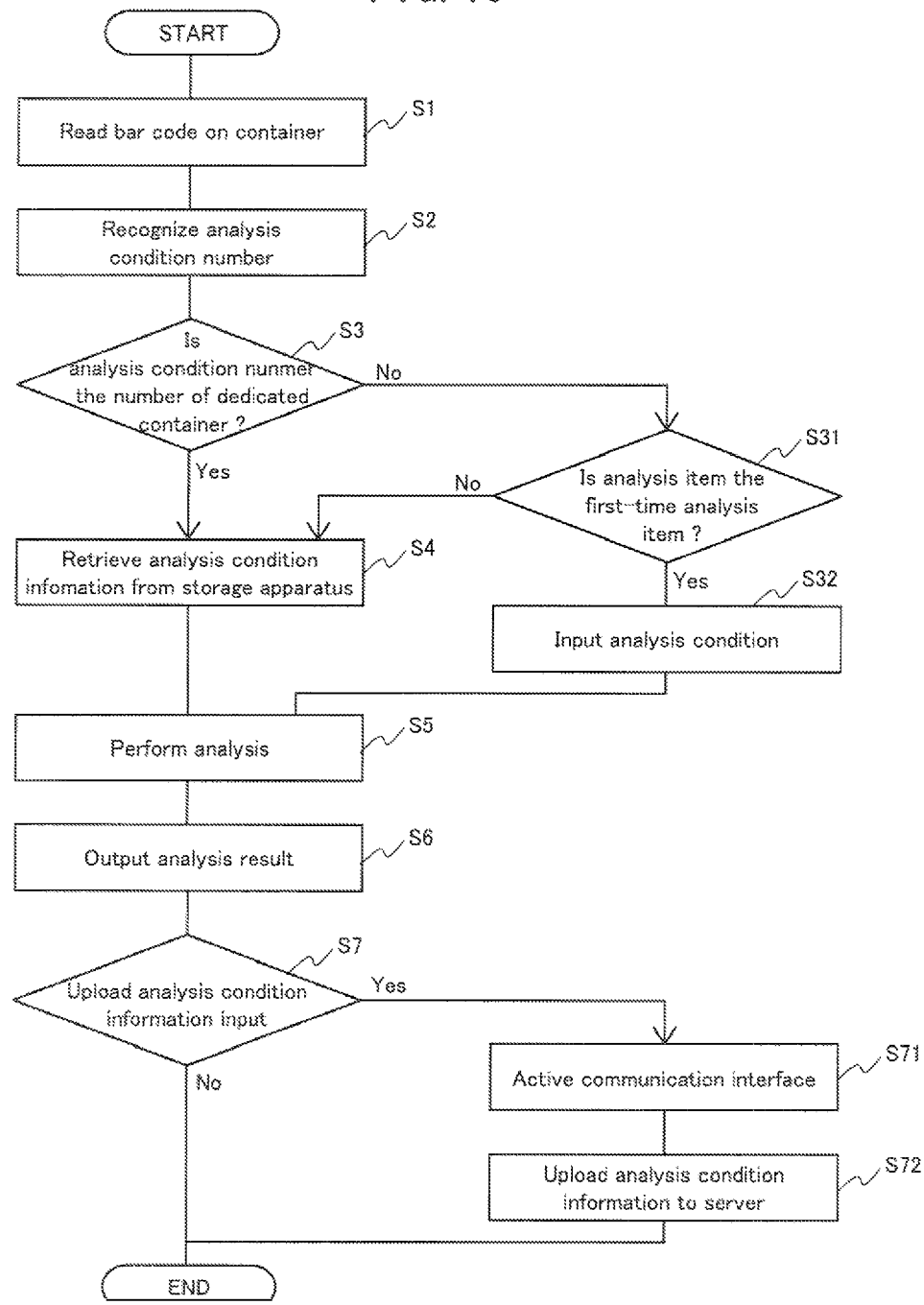
FIG. 10 is a flowchart showing yet another example of the analyzing system of the present invention.

With reference to a flowchart of FIG. 10, an example of an analyzing apparatus from which analysis condition information input by a user is uploaded to a server outside of the apparatus is explained. The analyzing apparatus of the present example has the same configuration as that of the analyzing apparatus of Example 2 (see FIG. 6). As shown in FIG. 10, in the analyzing apparatus of the present example, a procedure until outputting an analysis result is the same as that of the analyzing apparatus of Example 1 (see FIG. 8). Thus, in FIG. 10, the parts identical to those in FIG. 8 are denoted by the identical reference numerals. In the flowchart of FIG. 10, after outputting an analysis result (S6), information that causes a user to determine whether or not the input analysis condition information is uploaded is output to an output apparatus (S7). When the user selects not to upload the information (No), the measurement is completed. On the other hand, when the user selects to upload the information (Yes), a communication interface is activated by a CPU (S71), the analysis condition is uploaded to a server outside of the apparatus (S72), and an analysis is completed. In this analyzing apparatus, in the case where a server (a site) to which analysis condition information is uploaded is specified, a lot of analysis condition information is collected. In the case where an analysis item is set by a user for the first time as explained in the example of the analyzing apparatus of Example 2, downloading analysis condition information becomes easily. In the present example, whether or not analysis condition information is uploaded is selected after outputting an analysis result (S6). However, the present invention is not limited to this, and for example, whether or not an analysis condition is uploaded may be determined after performing the analysis (S5).

Example 4

Figure 11:
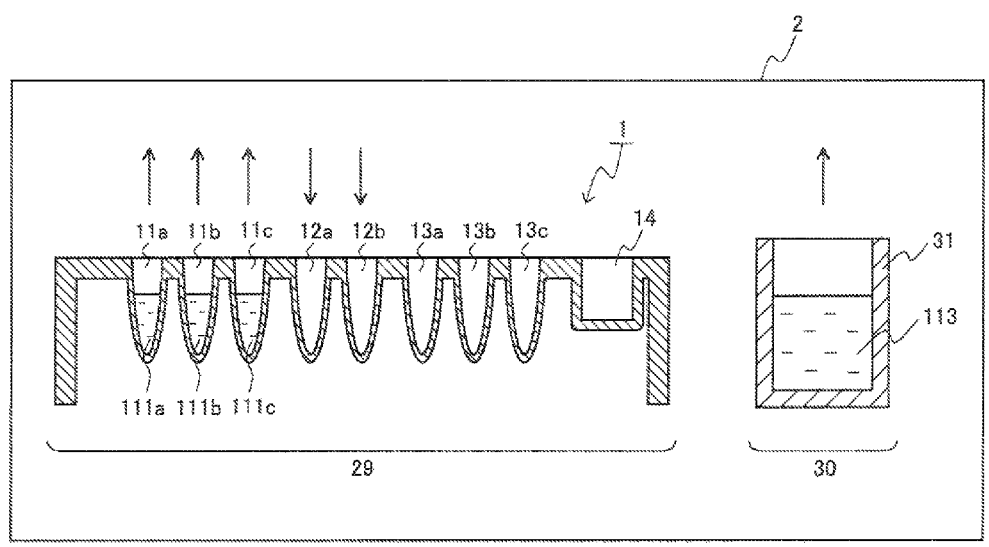
FIG. 11 is an illustration explaining an operation of an analyzing apparatus used in the analyzing system of the present invention.

With reference to FIG. 11, the example of an analyzing system using a cartridge-type expansion container and a specific reagent container is explained. In FIG. 11, the parts identical to those in FIGS. 1 to 4 are denoted by the identical reference numerals. As shown in FIG. 11, in the present example, a cartridge-type expansion container 1 and a specific reagent container 31 are used, and an analyzing apparatus 2 is provided with a cartridge-type expansion container setting part 29 and a specific reagent container setting part 30. Common reagent baths 11a, 11b, and 11c of the cartridge-type expansion container has been filled with common reagents 111a, 111b, and 111c, respectively, while specific reagent baths 13a, 13b, and 13c are empty. A specific reagent container 31 has been filled with a specific reagent 113.

An example of controlling an analysis in the analyzing system of the present example is explained by taking a case in which an analyte is a gene as an example. In the cartridge-type container, a common reagent bath 11 has been filled with dNTP, polymerase, and the other reagent, and a specific reagent container 31 has been filled with a primer and a probe. First, a user introduces a sample (a specimen) into a sample (a specimen) bath 14 of the cartridge-type container. Once this cartridge-type container is set in the analyzing apparatus, a nozzle automatically moves and samples a sample in the sample bath 14, and then introduces it into the operation bath 12. Subsequently, the nozzle automatically moves and samples the common reagents such as dNTP and polymerase, and then introduces them into the operation bath 12. Similarly, the nozzle automatically moves and samples the primer and the probe from the specific reagent container 31, and then introduces them into the operation bath 12. Thus, they react with the sample. In the case where the reaction is a PCR, a temperature cycle is controlled by the measurement unit. After the certain number of cycles of reactions, the probe in a reactant is detected by an optical manner. As described above, using a specific reagent container without using a specific reagent bath of a cartridge-type container enables saving an amount of a specific reagent to be used. For the sampling with a nozzle, an excess amount (a dead volume) to enable sampling is required besides an amount to be required for a reaction. In the cartridge-type container, in the case where, for example, four baths are filled with the same reagent for four times of measurements, for example, the total dead volume becomes 80 µL, i.e., 20 µL×four reagent baths, assuming that the amount to be required for a reaction is 20 µL, and the excess amount (the dead volume) to enable sampling is 20 µL. In contrast, by the use of a specific reagent container, the reagent amount to be required for four times of measurement becomes 80 µL (20 µL×four times of measurements), and the excess amount (the dead volume) to enable sampling becomes 20 µL. Thus, the total death volume can be 20 µL.

INDUSTRIAL APPLICABILITY

The analyzing system and the like of the present invention are used preferably in the field of clinical examination, but the present invention is not limited to this and can be widely applied to other fields.

The invention claimed is:

1. An analyzing system, comprising:
a container; and
an analyzing apparatus,
wherein the container is a dedicated container containing a reagent for a specific analysis item or an expansion container in which a user can freely set an analysis item, each of the dedicated container and the expansion container including an information label, where the information label includes analysis condition information by which identification of the container as the dedicated container or the expansion container can be determined, and
wherein the analyzing apparatus comprises:
a label reading device configured to read information on the information label; and
a controlling device configured to control an analysis condition, the controlling device determining whether the container is the dedicated container or the expansion container based on the analysis condition information of the information label,
wherein the expansion container includes a common reagent bath and a specific reagent bath.

2. The analyzing system according to claim 1,
wherein
the analysis condition information includes an analysis condition number and an analysis condition associated with the analysis condition number,
a corresponding analysis condition number is assigned to each of the dedicated container and the expansion container, and
the controlling device is configured to determine whether the container is the dedicated container or the expansion container based on the analysis condition number.

3. The analyzing system according to claim 1,
wherein the analyzing apparatus further comprises:
an analysis condition information storing device for storing analysis condition information with respect to each analysis item,
when the controlling device determines that the container is the dedicated container, the analysis condition information that is previously stored is retrieved from the analysis condition information storing device, and control information is output in accordance with the analysis condition information retrieved,
when the controlling device determines that the container is the expansion container, whether or not the analysis item that is set by a user is the first-time analysis item is determined,
when it is determined that the analysis item is the first-time analysis item, analysis condition input request information is output, and the analysis condition information that is input in accordance with the output information is stored in the analysis condition information storing device, and
when it is determined that the analysis item is not the first-time analysis item, control information is output in accordance with the analysis condition information that is stored in the analysis condition storing device.

4. The analyzing system according to claim 1,
wherein the analyzing apparatus further comprises:
an input device for inputting information from outside of the analyzing apparatus, and
the analysis condition information is input by the input device.

5. The analyzing system according to claim 1,
wherein the analyzing apparatus further comprises:
an information retrieving device,
the analysis condition information outside of the analyzing apparatus is retrieved through the communication network outside of the analyzing system by the information retrieving device in accordance with the analysis condition input request information, and the analysis condition information retrieved is input.

6. The analyzing system according to claim 5, further comprising:
a server storing the analyzing condition information outside of the analyzing apparatus.

7. The analyzing system according to claim 6,
wherein the analyzing apparatus further comprises:
an information transmitting device, and
analysis condition information that is related to an analysis item set by a user can be stored in the server through a communication network by the information transmitting device.

8. The analyzing system according to claim 1, wherein the specific reagent bath of the expansion container contains a specific reagent.

9. The analyzing system according to claim 1, wherein the analysis item is a gene, the common reagent contains DNA polymerase and dNTP, and the specific reagent contains a primer.

10. The analyzing system according to claim 1, wherein each of the dedicated container and the expansion container is a cartridge-type container.

11. The analyzing system according to claim 10, further comprising:
a specific reagent container contain a specific reagent to be provided depending on the analysis item that is set by a user, wherein
the analyzing apparatus includes the cartridge-type container setting part and the specific reagent container setting part.

12. The analyzing system according to claim 11, wherein in the analyzing apparatus,
the cartridge-type expansion container is set in the cartridge-type container setting part,
the specific reagent container is set in the specific reagent container setting part, the cartridge-type expansion container includes a common reagent bath to contain a common reagent, and
the specific reagent container is to contain the specific reagent.

13. The analyzing system according to claim 1, wherein the information label is a bar code or a two-dimensional code.

14. An analyzing system, comprising:
a container; and
an analyzing apparatus,
wherein the container is a dedicated container containing a reagent for a specific analysis item or an expansion container in which a user can freely set an analysis item, each of the dedicated container and the expansion container including an information label, where the information label includes analysis condition information by which identification of the container as the dedicated container or the expansion container can be determined, and
wherein the analyzing apparatus comprises:
a label reading device configured to read information on the information label;
an analysis condition information storing device configured to store analysis condition information with respect to each analysis item;
an input device configured to input the analysis condition information and information from outside of the analyzing apparatus; and
a controlling device configured to control an analysis condition, the controlling device determining whether the container is the dedicated container or the expansion container based on the analysis condition information of the information label,
wherein
when the controlling device determines that the container is the dedicated container, the analysis condition information previously stored is retrieved from the analysis condition information storing device, and control information is output in accordance with the analysis condition information retrieved,
when the controlling device determines that the container is the expansion container, determining whether the analysis item set by a user is the first-time analysis item,
when the analysis item is the first-time analysis item, analysis condition input request information is output, and the analysis condition information input in accordance with the output information is stored in the analysis condition information storing device, and
when the analysis item is not the first-time analysis item, control information is output in accordance with the analysis condition information stored in the analysis condition storing device.

* * * * *